United States Patent
Gibson et al.

(10) Patent No.: US 6,683,141 B1
(45) Date of Patent: Jan. 27, 2004

(54) POLYMERIZATION CATALYSTS

(75) Inventors: Vernon Charles Gibson, London (GB); Brian Stephen Kimberley, Sunbury on Thames (GB); Gregory Adam Solan, Hornchurch (GB)

(73) Assignee: BP Chemicals Limited, London (GB)

( * ) Notice: Subject to any disclaimer, the term of this patent is extended or adjusted under 35 U.S.C. 154(b) by 132 days.

(21) Appl. No.: 09/702,745

(22) Filed: Nov. 1, 2000

Related U.S. Application Data

(63) Continuation of application No. PCT/GB99/03152, filed on Sep. 22, 1999.

(30) Foreign Application Priority Data

| Oct. 2, 1998 | (GB) | ............................................. 9821542 |
| Dec. 23, 1998 | (GB) | ............................................. 9828546 |
| Jun. 19, 1999 | (GB) | ............................................. 9914336 |

(51) Int. Cl.$^7$ ............................. C08F 4/44; B01J 31/18
(52) U.S. Cl. ...................... 526/161; 526/172; 502/155; 502/167; 556/13; 556/51; 556/136; 556/138; 546/20
(58) Field of Search ................................ 526/161, 172; 502/155, 156, 167, 168; 556/51, 136, 138, 13; 546/21

(56) References Cited

U.S. PATENT DOCUMENTS 6,133,387 A * 10/2000 Xu et al. .................... 526/172

FOREIGN PATENT DOCUMENTS

WO    WO 98/27124    *   6/1998

OTHER PUBLICATIONS

M. Bruce et al., "Cationic Alkyl Aluminium Ethylene Polymerization Catalysts Based on Monoanionic N, N, N,–Pyridyliminoamide Ligands", Chem. Commun., pp. 2523–2524, (1998).

V.C. Gibson et al., "Synthesis and Structural Characterisation of Aluminium Imino–Amide and Pyridyl–Amide Complexes: Bulky Monoanionic N,N Chelate Ligands Via Methyl Group Transfer", Journal of Organometallic Chemistry, vol. 550, pp. 453–456, (1998).

S. Midollini et al., "Oxomolybdenum(IV) and Oxovanadium(IV) Complexes with a Tridentate Schiff Base", J. Chem Soc. (A), pp. 2964–2966, (1970).

* cited by examiner

Primary Examiner—Robert Deshon Harlan
(74) Attorney, Agent, or Firm—Finnegan, Henderson, Farabow, Garrett and Dunner, L.L.P.

(57) ABSTRACT

A complex suitable for the polymerization of 1-olefins is disclosed, having the Formula A

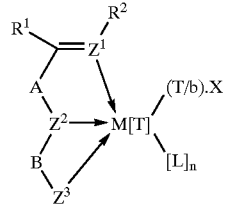

(Formula A)

wherein M is a transition metal, lanthanide or actinide; X represents an atom or group covalently or ionically bonded to the transition metal M; b is the valency of the atom or group X; $Z^1$ is N or P; $Z^2$ is N, P, $N^-$, $P^-$ or $NR^5$; $Z^3$ is one of N, P, O, S, $NHR^3$, $NR^3R^4$, OH, $OR^3$, SH, $SR^3$, $PHR^3$, $PR^3R^4$, $(NR^3)^-$, $O^-$, $S^-$, $(PR^3)^-$, $P(R^3R^4)O$, $NR^3$ or $PR^3$ to the proviso that one of $Z^2$ and $Z^3$ is anionic; T is the oxidation state of the transition metal M when both $Z^2$ or $Z^3$ are neutral, and is one less than the oxidation state of M when one of $Z^2$ or $Z^3$ is anionic; A and B are independently hydrocarbyl, substituted hydrocarbyl, heterohydrocarbyl or substituted heterohydrocarbyl, and may together with $Z^2$ form part of a heterocyclic substituent; B may be joined to $Z^3$ by either a single or a double bond; $R^1$ to $R^5$ are each independently selected from hydrogen, halogen, hydrocarbyl, substituted hydrocarbyl, heterohydrocarbyl or substituted heterohydrocarbyl, and any two or more of $R^1$ to $R^5$ when hydrocarbyl may be joined together to form a ring; L is a solvate molecule, and n is from 0 to 5. The complex is useful as a polymerization catalyst in a process for the polymerization and copolymerization of olefins.

36 Claims, No Drawings

POLYMERIZATION CATALYSTS

This application is a Continuation of International Application Number PCT/GB99/03152, filed Sep. 22, 1999.

The present invention relates to transition metal complex compounds, to polymerisation catalysts based thereon and to their use in the polymerisation and copolymerisation of olefins.

The use of certain transition metal compounds to polymerise 1-olefins, for example, ethylene or propylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the. produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

In recent years the use of certain metallocene catalysts (for example biscyclopentadienylzirconiumdichloride activated with alumoxane) has provided catalysts with potentially high activity. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

Patent Application WO98/27124 discloses that ethylene may be polymerised by contacting it with certain iron or cobalt complexes of selected 2,6-pyridinecarboxaldehydebis (imines) and 2,6-diacylpyridinebis(imines). In J. Chem. Soc. (A), 1970, 2964–2966, oxovanadium (IV) complexes of the general formula VO[2,6-bis-(1-(phenylimino)ethyl) pyridine]$X_2$ where X is Cl or Br are disclosed, but no polymerisation utility is mentioned.

An object of the present invention is to provide a novel catalyst suitable for polymerising and oligomerising monomers, for example, olefins such as α-olefins containing from 2 to 20 carbon atoms, and especially for polymerising ethylene alone, propylene alone, or for copolymerising ethylene or propylene with other 1-olefins such as $C_{2-20}$ α-olefins. A fuirther object of the invention is to provide an improved process for the polymerisation of olefins, especially of ethylene alone or the copolymerisation of ethylene or propylene with higher 1-olefins to provide homopolymners and copolymers having controllable molecular weights. For example, using the catalysts of the present invention there can be made a wide variety of products such as, for example, liquid polyolefins, oligomers, linear α-olefins, branched α-olefins, resinous or tacky polyolefins, solid polyolefins suitable for making flexible film and solid polyolefins having high stiffness.

The present invention provides a transition metal complex having the Formula A

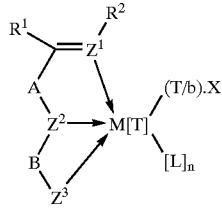

(Formula A)

wherein M is a transition metal, lanthanide or actinide; X represents an atom or group covalently or ionically bonded to the transition metal M; b is the valency of the atom or group X; $Z^1$ is N or P; $Z^2$ is N, P, $N^-$, $P^-$ or $NR^5$; $Z^3$ is one of N P, O, S, $NHR^3$, $NR^3R^4$, OH, $OR^3$, SH, $SR^3$, $PHR^3$, $PR^3R^4$, $(NR^3)^-$, $O^-$, $S^-$, $(PR^3)^-$, $P(R^3R^4)O$, $NR^3$ or $PR^3$, subject to the proviso that the ligand joined to M via $Z^1$, $Z^2$ and $Z^3$ is monoanionic or neutral, and that when neutral it is not a pyridyl diimine ligand; T is the oxidation state of the transition metal M when both $Z^2$ and $Z^3$ are neutral, and 1 less than the oxidation state of M when one of $Z^2$ or $Z^3$ is anionic; A and B are independently hydrocarbyl, substituted hydrocarbyl, heterohydrocarbyl or substituted heterohydrocarbyl, and may together with $Z^2$ form part of a heterocyclic substituent; B may be joined to $Z^3$ by either a single or a double bond; $R^1$ to $R^5$ are each independently selected from hydrogen, halogen, hydrocarbyl, substituted hydrocarbyl, heterohydrocarbyl or substituted heterohydrocarbyl, and any two or more of $R^1$ to $R^5$ when hydrocarbyl may be joined together to form a ring; L is a solvate molecule, and n is from 0 to 5.

In a preferred embodiment either $Z^2$ or $Z^3$ is $N^-$ and is joined to M by a covalent bond.

Preferably M is Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[(III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV] or Nb[V].

Preferably the complex of the invention comprises the skeletal unit shown in Formula B

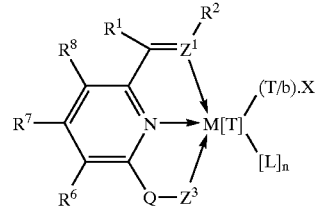

Formula B wherein M is Ti[II], Ti[III], TI[IV], Fe[II], Fe[III], Co[II], Co[III], Ni[II], Cr[II], Cr[III], Mn[II], Mn[III], Mn[IV], Ru[II], Ru[III], Ru[IV], Pd[II], Zr[II], Zr[III], Zr[IV], Hf[II], Hf[III], Hf[IV], V[II], V[III], V[IV], Nb[II], Nb[III], or Nb[IV]; X represents an atom or group covalently or ionically bonded to the transition metal M; b is the valency of the atom or group X; $Z^1$ is N or P; $Z^3$ is one of $NHR^3$, $NR^3R^4$, OH, $OR^3$, SH, $SR^3$, $PHR^3$, $PR^3R^4$, $(NR^3)^-$, $O^-$, $S^-$, $(PR^3)^-$ or $P(R^3R^4)O$; T is the oxidation state of the transition metal M when $Z^3$ is neutral, and 1 less than the oxidation state of M when $Z^3$ is anionic; Q is joined to $Z^3$ by a single bond and is hydrocarbyl, substituted hydrocarbyl, heterohydrocarbyl or substituted heterohydrocarbyl, preferably —$C(R^9)(R^{10})$—; $R^1$ to $R^{10}$ are each independently selected from hydrogen, halogen, hydrocarbyl, substituted hydrocarbyl, heterohydrocarbyl or substituted heterohydrocarbyl, and when hydrocarbyl any two or more of $R^1$ to $R^{10}$ may be joined together to form a ring; L is a solvate molecule, and n is from 0 to 5, preferably 0.

In a preferred embodiment $R^2$ is preferably represented by the structure

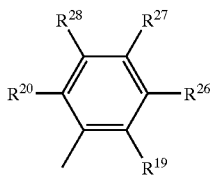

and $R^3$ by the structure

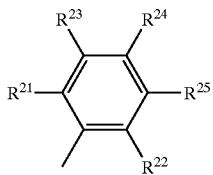

wherein $R^{19}$ to $R^{28}$ are each independently selected from hydrogen, halogen, hydrocarbyl, substituted hydrocarbyl, heterohydrocarbyl or substituted heterohydrocarbyl, and when hydrocarbyl any two or more thereof may be joined together to form a ring.

$R^6$ to $R^{28}$ are preferably independently selected from hydrogen and $C_1$ to $C_8$ hydrocarbyl, for example, methyl, ethyl, n-propyl, iso-propyl, n-butyl, sec-butyl, tert.-butyl, n-pentyl, neopentyl, n-hexyl, 4-methylpentyl, n-octyl, phenyl and benzyl. In particular at least one of $R^{24}$ and $R^{27}$ may contain two carbon atoms, preferably 4 to 8 carbon atoms.

Preferably at least one of $R^{19}$, $R^{20}$, $R^{21}$ and $R^{22}$ is hydrocarbyl, substituted hydrocarbyl, heterohydrocarbyl or substituted heterohydrocarbyl. More preferably at least one of $R^{19}$ and $R^{20}$, and at least one of $R^{21}$ and $R^{22}$, is hydrocarbyl, substituted hydrocarbyl, heterohydrocarbyl or substituted heterohydrocarbyl. Most preferably $R^{19}$, $R^{20}$, $R^{21}$ and $R^{22}$ are all independently selected from hydrocarbyl, substituted hydrocarbyl, heterohydrocarbyl or substituted heterohydrocarbyl. $R^{19}$, $R^{20}$, $R^{21}$ and $R^{22}$ are preferably independently selected from methyl, ethyl, n-propyl, iso-propyl, n-butyl, sec-butyl, tert.-butyl, n-pentyl, neopentyl, n-hexyl, 4-methylpentyl, n-octyl, phenyl and benzyl.

$R^1$ to $R^5$ are independently preferably $C_1$–$C_{16}$ hydrocarbyl, particularly $C_6$–$C_{16}$ alkylphenyl. Preferred aryl groups include 2,4,6-trimethylphenyl, 2,6-diisopropylphenyl, 2,6-dimethyl-4-tert.butyl-phenyl, 2,6-dimethylphenyl, 2-methylphenyl, 2,4-dimethylphenyl, 2,3-dimethylphenyl, 2-ethylphenyl, 2-isopropylphenyl, and 2-tert.butyl.

In one embodiment $Z^3$ is $(NR^3)^-$or $O^-$, and $R^3$ is preferably as defined in the paragraph above.

In the complex of the present invention the transition metal M is preferably Fe[II], Fe[III], Co[II], Co[III] or Zr(IV).

$Z^1$ is preferably N, and more preferably $Z^1$, $Z^2$ and $Z^3$ are all N. $Z^2$ when it is N is coordinated to the transition metal M by a "dative" bond, ie a bond formed by donation of a lone pair of electrons from the nitrogen atom. The remaining bonds on the atom are covalent bonds formed by electron sharing between the nitrogen and the organic ligand as shown in the defined formula for the transition metal complex illustrated above. $Z^1$ and $Z^3$ are coordinated to the transition metal M by a "dative" bond when neutral, and by a covalent bond if anionic.

The atom or group represented by X can be, for example, selected from halide, sulphate, nitrate, thiolate, thiocarboxylate, $BF_4^-$, $PF_6^-$, hydride, hydrocarbyloxide, carboxylate, hydrocarbyl, substituted hydrocarbyl and heterohydrocarbyl. Examples of such atoms or groups are chloride, bromide, methyl, ethyl, propyl, butyl, octyl, decyl, phenyl, benzyl, methoxide, ethoxide, isopropoxide, tosylate, triflate, formate, acetate, phenoxide and benzoate. Preferred examples of the atom or group X are halide, for example, chloride, bromide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl. Chloride is particularly preferred.

The solvate molecule L may be an ether such as tetrahydrofuran or diethylether, and alcohol such as ethanol or butanot, a primary, secondary or tertiary amine, or a phosphine.

Examples of complexes of the present invention include
2-formyl(2,6-diisopropylylanil),6-[(2,6-diisopropylphenyl)amino](methyl)methyl-pyridine.FeCl$_2$ 2-formyl(2,4,6-trimethylanil),6-[(2,4,6-trimethylphenyl)amino](methyl)methyl-pyridine.FeCl$_2$ 2-formyl(2-tert.butylanit),6-[(2-tert.butylphenyl)amino](methyl)methyl-pyridine.FeCl$_2$ 2-formyl(2,6-diisopropylylanil),6-[(2,6-diisopropylphenyl)amino](methyl)methyl-pyridine.FeBr$_2$ 2-acetyl(2,6-diisopropylylani),6-[(2,6-diisopropylphenyl)amino](dimethyl) methyl-pyridine.FeCl$_2$ 2-formyl(2,6-diisopropylylanil),6-[(2,6-diisopropylphenyl)amino](methyl)methyl-pyridine.CoCl$_2$ 2-formyl(2,6-diisopropylylanil),6-[(2,6-diisopropylphenyl)amino](methyl)methyl-pyridine.CrCl$_2$ 2-formyl(2,6-diisopropylylanil),6-[(2,6-diisopropylphenyl)amino](methyl)methyl-pyridine.Zr(NMe$_2$)$_3$ 2-acetyl(2,6-diisopropylylanil),6-(dimethyl)methanol-pyridine.FeCl2

2-acetyl(2,6-diisopropylylanil),6-(dimethyl)methanol-pyridine.CoCl$_2$ 2-acetyl(2,4,6-trimethylanfl),6-[(2,4,6-trimethylphenyl)amido]n-butyl)methyl-pyridine.FeCl 2-acetyl(2,4,6-trimethylanil),6-[(2,4,6-trimethylphenyl)amido]n-butyl)methyl-pyridine.CoCl.

The present invention further provides a polymerisation catalyst comprising
(1) a compound having the Formula A as hereinbefore defined, and
(2) an activating quantity of at least one activator compound.

The activator compound for the catalyst of the present invention is suitably selected from organoaluminium compounds and hydrocarbylboron compounds. Suitable organoaluminium compounds include compounds of the formula AlR3, where each R is independently $C_1$–$C_{12}$ alkyl or halo. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof. Commercially available alumoxanes are generally believed to be mixtures of linear and cyclic compounds. The cyclic alumoxanes can be represented by the formula $[R^{16}AlO]_s$ and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups. Alkylalumoxanes such as methylalumoxane (MAO) are preferred.

Mixtures of alkylalumoxanes and trialkylaluminium compounds are particularly preferred, such as MAO with TMA or TIBA. In this context it should be noted that the term "alkylalumoxane" as used in this specification includes alkylalumoxanes available commercially which may contain a proportion, typically about 10 wt %, but optionally up to 50 wt %, of the corresponding trialkylaluminium; for instance, commercial MAO usually contains approximately 10 wt % trimethylaluminium (TMA), whilst commercial MMAO contains both TMA and TIBA. Quantities of alkylalumoxane quoted herein include such trialkylaluminium impurities, and accordingly quantities of trialkylaluminium compounds quoted herein are considered to comprise compounds of the formula $AlR_3$ additional to any $AlR_3$ compound incorporated within the alkylalumoxane when present.

Examples of suitable hydrocarbylboron compounds are boroxines, trimethylboron, triethylboron, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)[(bis-3,5-trifluoromethyl)phenyl]borate$, trityltetra(pentafluorophenyl)borate and tris(pentafluorophenyl)boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per atom of metal M in the compound of Formula (I).

An alternative class of activators comprise salts of a cationic oxidising agent and a non-coordinating compatible anion. Examples of cationic oxidising agents include: ferrocenium, hydrocarbyl-substituted ferrocenium, $Ag^+$, or $Pb^{2+}$. Examples of non-coordinating compatible anions are $BF_4^-$, $SbCl_6^-$, $PF_6^-$, tetrakis(phenyl)borate and tetrakis(pentafluorophenyl)borate.

A further aspect of the present invention provides a polymerisation catalyst system comprising (1) a compound of the Formula A, (2) an activating quantity of at least one activator compound selected from organoaluminium and hydrocarbylboroncompounds, and (3) a neutral Lewis base.

Neutral Lewis bases are well known in the art of Ziegler-Natta catalyst polymerisation technology. Examples of classes of neutral Lewis bases suitably employed in the present invention are unsaturated hydrocarbons, for example, alkenes (other than 1-olefins) or alkynes, primary, secondary and tertiary amines, amides, phosphoramides, phosphines, phosphites, ethers, thioethers, nitriles, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2) and (3) of the catalyst system can be brought together simultaneously or in any desired order. However, if components (2) and (3) are compounds which interact together strongly, for example, form a stable compound together, it is preferred to bring together either components (1) and (2) or components (1) and (3) in an initial step before introducing the final defined component. Preferably components (1) and (3) are contacted together before component (2) is introduced. The quantities of components (1) and (2) employed in the preparation of this catalyst system are suitably as described above in relation to the catalysts of the present invention. The quantity of the neutral Lewis Base [component (3)] is preferably such as to provide a ratio of component (1):component (3) in the range 100:1 to 1:1000, most preferably in the range 1:1 to 1:20. Components (1), (2) and (3) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures e.g. up to 120° C. can be carried out if desired, e.g. to achieve better mixing of the components. It is preferred to carry out the bringing together of components (1), (2) and (3) in an inert atmosphere (e.g. dry nitrogen) or in vacuo. If it is desired to use the catalyst on a support material (see below), this can be achieved, for example, by preforrning the catalyst system comprising components (1), (2) and (3) and impregnating the support material preferably with a solution thereof, or by introducing to the support material one or more of the components simultaneously or sequentially. If desired the support material itself can have the properties of a neutral Lewis base and can be employed as, or in place of, component (3). An example of a support material having neutral Lewis base properties is poly(aminostyrene) or a copolymer of styrene and arminostyrene (ie vinylaniline).

The catalysts of the present invention can if desired comprise more than one of the defined compounds. Alternatively, the catalysts of the present invention can also include one or more other types of transition metal compounds or catalysts, for example, nitrogen containing catalysts such as those described in our copending application WO 99/12981. Examples of such other catalysts include 2,6-diacetylpyridinebis(2,4,6-trimethyl anil)FeCl$_2$.

The catalysts of the present invention can also include one or more other types of catalyst, such as those of the type used in conventional Ziegler-Natta catalyst systems, metallocene-based catalysts, monocyclopentadienyl- or constrained geometry based catalysts, or heat activated supported chromium oxide catalysts (eg Phillips-type catalyst).

The catalysts of the present invention can be unsupported or supported on a support material, for example, silica, alumina, MgCl$_2$ or zirconia, or on a polymer or prepolymer, for example polyethylene, polypropylene, polystyrene, or poly(aminostyrene).

If desired the catalysts can be formed in situ in the presence of the support material, or the support material can be pre-impregnated or premixed, simultaneously or sequentially, with one or more of the catalyst components. The catalysts of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

The present invention further provides a process for the polymerisation and copolymerisation of 1-olefins, comprising contacting the monomeric olefin under polymerisation conditions with the polymerisation catalyst or catalyst system of the present invention. A preferred process comprises the steps of:

a) preparing a prepolymer-based catalyst by contacting one or more 1-olefins with a catalyst system, and b) contacting the prepolymer-based catalyst with one or more 1-olefins, wherein the catalyst system is as defined above.

In the text hereinbelow, the term "catalyst" is intended to include "catalyst system" as defined previously and also "prepolymer-based catalyst" as defined above.

The polymerisation conditions can be, for example, solution phase, slurry phase, gas phase or bulk phase, with polymerisation temperatures ranging from −100° C. to +300° C., and at pressures of atmospheric and above, particularly from 140 to 4100 kPa. If desired, the catalyst can be used to polymerise ethylene under high pressure/high temperature process conditions wherein the polymeric material forms as a melt in supercritical ethylene. Preferably the polymerisation is conducted under gas phase fluidised bed or stirred bed conditions.

Suitable monomers for use in the polymerisation process of the present invention are, for example, ethylene and C$_{2-20}$ α-olefins, specifically propylene, 1-butene, 1-pentene, 1-hexene, 4-methylpentene-1, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene. Other monomers include methyl methacrylate, methyl acrylate, butyl acrylate, acrylonitrile, vinyl acetate, and styrene. Preferred monomers for homopolymerisation processes are ethylene and propylene.

The catalysts and process of the invention can also be used for copolymerising ethylene or propylene with each other or with other 1-olefins such as 1-butene, 1-hexene, 4-methylpentene-1, and octene, or with other monomeric materials, for example, methyl methacrylate, methyl acrylate, butyl acrylate, acrylonitrile, vinyl acetate, and styrene.

Irrespective of the polymerisation or copolymerisation technique employed, polymerisation or copolymerisation is typically carried out under conditions that substantially exclude oxygen, water, and other materials that act as catalyst poisons. Also, polymerisation or copolymerisation can be carried out in the presence of additives to control polymer or copolymer molecular weights.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase, bulk phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of complex employed in the catalyst system). This means that relatively very small quantities of transition metal complex are consumed in commercial processes using the process of the present invention. It also means that when the polymerisation process of the present invention is operated under polymer recovery conditions that do not employ a catalyst separation step, thus leaving the catalyst, or residues thereof, in the polymer (e.g. as occurs in most commercial slurry and gas phase polymerisation processes), the amount of transition metal complex in the produced polymer can be very small.

Slurry phase polymerisation conditions or gas phase polymerisation conditions are particularly useful for the production of high or low density grades of polyethylene, and polypropylene. In these processes the polymerisation conditions can be batch, continuous or semi-continuous. Furthermore, one or more reactors may be used, e.g. from two to five reactors in series. Different reaction conditions, such as different temperatures or hydrogen concentrations may be employed in the different reactors. In the slurry phase process and the gas phase process, the catalyst is generally metered and transferred into the polymerisation zone in the form of a particulate solid either as a dry powder (e.g. with an inert gas) or as a slurry. This solid can be, for example, a solid catalyst system formed from the one or more of complexes of the invention and an activator with or without other types of catalysts, or can be the solid catalyst alone with or without other types of catalysts. In the latter situation, the activator can be fed to the polymerisation zone, for example as a solution, separately from or together with the solid catalyst. Preferably the catalyst system or the transition metal complex component of the catalyst system employed in the slurry polymerisation and gas phase polymerisation is supported on one or more support materials.

Most preferably the catalyst system is supported on the support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques. Once the polymer product is discharged from the reactor, any associated and absorbed hydrocarbons are substantially removed, or degassed, from the polymer by, for example, pressure letdown or gas purging using fresh or recycled steam, nitrogen or light hydrocarbons (such as ethylene). Recovered gaseous or liquid hydrocarbons may be recycled to the polymerisation zone.

In the slurry phase polymerisation process the solid particles of catalyst, or supported catalyst, are fed to a polymerisation zone either as dry powder or as a slurry in the polymerisation diluent. The polymerisation diluent is compatible with the polymer(s) and catalyst(s), and may be an alkane such as hexane, heptane, isobutane, or a mixture of hydrocarbons or paraffins. Preferably the particles are fed to a polymerisation zone as a suspension in the polymerisation diluent, The polymerisation zone can be, for example, an autoclave or similar reaction vessel, or a continuous loop reactor, e.g. of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a usefuil means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

In bulk polymerisation processes, liquid monomer such as propylene is used as the polymerisation medium.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid in the polymerisation zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

For typical production of impact copolymers, homopolymer formed from the first monomer in a first reactor is reacted with the second monomer in a second reactor. For manufacture of propylene/ethylene impact copolymer in a gas-phase process, propylene is polymerized in a first reactor; reactive polymer transferred to a second reactor in which ethylene or other comonomer is added. The result is an intimate mixture of a isotactic polypropylene chains with chains of a random propylene/ethylene copolymer. A random copolymer typically is produced in a single reactor in which a minor amount of a comonomer (typically ethylene) is added to polymerizing chains of propylene.

Methods for operating gas phase fluidised bed processes for making polyethylene, ethylene copolymers and polypropylene are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen or inert hydrocarbons such as methane, ethane, propane, butane, pentane or hexane) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and then returned to the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

Although not usually required, upon completion of polymerisation or copolymerisation, or when it is desired to terminate polymerisation or copolymerisation or at least temporarily deactivate the catalyst or catalyst component of this invention, the catalyst can be contacted with water, alcohols, acetone, or other suitable catalyst deactivators a manner known to persons of skill in the art.

Homopolymerisation of ethylene with the catalysts of the invention may produce so-called "high density" grades of polyethylene. These polymers have relatively high stiffness and are useful for making articles where inherent rigidity is required. Copolymerisation of ethylene with higher 1-olefins (eg butene, hexene or octene) can provide a wide variety of copolymers differing in density and in other important physical properties. Particularly important copolymers made by copolymerising ethylene with higher 1-olefins with the catalysts of the invention are the copolymers having a density in the range of 0.91 to 0.93. These copolymers which are generally referred to in the art as linear low density polyethylene, are in many respects similar to the so called low density polyethylene produced by the high pressure free radical catalysed polymerisation of ethylene. Such polymers and copolymers are used extensively in the manufacture of flexible blown film.

Propylene polymers produced by the process of the invention include propylene homopolymer and copolymers of propylene with less than 50 mole % ethylene or other alpha-olefin such as butene-1, pentene-1, 4-methylpentene-1, or hexene-1, or mixtures thereof. Propylene polymers also may include copolymers of propylene with minor amounts of a copolymerizable monomer. Typically, most useful are normally-solid polymers of propylene containing polypropylene crystallinity, random copolymers of propylene with up to about 10 wt. % ethylene, and impact copolymers containing up to about 20 wt. % ethylene or other alpha-olefin. Polypropylene homopolymers may contain a small amount (typically below 2 wt. %) of other monomers to the extent the properties of the homopolymer are not affected significantly.

Propylene polymers may be produced which are normally solid, predominantly isotactic, poly α-olefins. Levels of stereorandom by-products are sufficiently low so that useful products can be obtained without separation thereof, Typically, useful propylene homopolymers show polypropylene crystallinity and have isotactic indices above 90 and many times above 95. Copolymers typically will have lower isotactic indices, typically above 80–85.

Depending upon polymerisation conditions known in the art, propylene polymers with melt flow rates from below 1 to above 1000 may be produced in a reactor. For many applications, polypropylenes with a MFR from 2 to 100 are typical. Some uses such as for spunbonding may use a polymer with an MFR of 500 to 2000.

Peroxide compounds may be added to ethylene or propylene polymers. For ethylene based polymers, peroxides can be used to give cross-linking in the polymer. For the preparation of high MFR propylene polymers, peroxide compounds may be added during extrusion for controlled rheology to increase the melt flow rate of polymer. Peroxide acts to break long polymer chains and has the effect of both increasing MFR and narrowing the molecular weight distribution (Mw/Mn) or polydispersity. A typical reactor polypropylene powder with an MFR of 2 g/10 min. by controlled rheology treatment with peroxide in an extruder may form a polymer with an MFR of 20–40. By varying the type, amount of, and process conditions using, peroxide, the final polymer MFR may be controlled as known in the art.

Depending upon the use of the polymer product, minor amounts of additives are typically incorporated into the polymer formulation such as acid scavengers, antioxidants, stabilizers, and the like. Generally, these additives are incorporated at levels of about 25 to 2000 ppm, typically from about 50 to about 1000 ppm, and more typically 400 to 1000 ppm, based on the polymer.

In use, polymers or copolymers made according to the invention in the form of a powder are conventionally compounded into pellets. Examples of uses for polymer compositions made according to the invention include use to form fibres, extruded films, tapes, spunbonded webs, moulded or thernoformed products, and the like. The polymers may be blown into films, or may be used for making a variety of moulded or extruded articles such as pipes, and containers such as bottles or drums. Specific additive packages for each application may be selected as known in the art. Examples of supplemental additives include slip agents, anti-blocks, anti-stats, mould release agents, primary and secondary anti-oxidants, clarifiers, nucleants, uv stabilizers, and the like. Classes of additives are well known in the art and include phosphite antioxidants, hydroxylamine (such as N,N-dialkyl hydroxylamine) and amine oxide (such as dialkyl methyl amine oxide) antioxidants, hindered amine light (uv) stabilizers, phenolic stabilizers, benzofuiranone stabilizers, and the like. Various olefin polymer additives are described in U.S. Pat. Nos. 4,318,845, 4,325,863, 4,590,231, 4,668,721, 4,876,300, 5,175,312, 5,276,076, 5,326,802, 5,344,860, 5,596,033, and 5,625,090.

Fillers such as silica, glass fibers, talc, and the like, nucleating agents, and colourants also may be added to the polymer compositions as known by the art.

The present invention is illustrated in the following Examples.

Preparation of Ligands

EXAMPLE 1

Preparation of 2-formyl(2,6-diisopropylylanil),6-[(2.6-diisopropylphenyl)amino](methyl)methyl-pyridine 2a Compound 2a was prepared in a two-step procedure:

(1) The 2,6-bis(imino)pyridine, $C_5H_3(CHN(2.6\text{-}i\text{-}Pr_2\text{-}C_6H_3))_2$ (5.0 g, 0.011 mol) was dissolved in toluene (40 ml) and two equivalents of $AlMe_3$ (2.0 M, 11.0 ml, 0.022 mol) introduced. The reaction mixture was stirred at reflux for 12 hours. After removal of the volatiles acetonitrile (60 ml) was added and refluxed until dissolution. On cooling to room temperature large pale yellow crystals of $[C_5H_3(CHN(2,6\text{-}i\text{-}Pr_2\text{-}C_6H_3))(CHMeN(2,6\text{-}i\text{-}Pr_2\text{-}C_6H_3))]AlMe_2$ 1a formed which were filtered and collected.

(2) Pentane (40 ml) was added to 1a followed by slow addition of an equal volume of water. After stirring for a further 3 hours the pentane was stripped off. The aqueous phase was then extracted into chloroform (3×30 ml), filtered, dried over $MgSO_4$ and taken to dryness to give analytically pure 2a (4.14 g, 80%).

Compound 2a: Mass spectrum: m/z 469 [M$^+$]. $^1$H NMR (CDCl$_3$): d 8.38 [s, 1H, $C_5H_3C\underline{H}N$], 8.17[m, $C_5H_3N$, 1H], 7.72[m, $C_5H_3N$, 1H], 7.3–7.1[m, i-$Pr_2$ $C_6H_3$ & $C_5H_3N$, 7H], 4.48[d, $^3J(HH)$ 8., NH, 1H], 4.35[m, CHMe, 1H], 3.31[sept., CH Me$_2$], 3.02[sept., C$\underline{H}$Me$_2$], 1.49[d, $^3J(HH)$ 7, 3H, CH $\underline{Me}$] and 1.3–1.0 [m, 24H, CH Me$_2$].

EXAMLE 2

Preparation of 2-formyl(2,4,6-trimethylanil),6-[(2,4,6-trimethylphenyl)amino](methyl)methyl-pyridine 2b Compound 2b was prepared in analogous route to that outlined for 2a using $C_5H_3(CHN(2,4,6\text{-}Me_3\text{-}C_6H_2))_2$ (5.0 g, 0.014 mol) as the starting 2,6-bis(imino)pyridine Compound 2b was obtained analytically pure in good yield (3.91 g, 75%).

Compound 2b: Mass spectrum m/z 385 [M$^+$]. $^1$H NMR (CDCl$_3$): d 8.38.[s, 1H, $C_5H_3C\underline{H}N$], 8.16[m, $C_5H_3N$, 1H], 7.71[m, $C_5H_3N$, 1H], 7.23 [m, 1H, $C_5H_3N$], 7.0–6.7[m, 4H, Me$_3$- $C_6\underline{H}_2$], 4.5[m, CHMe, 1H], 4.35[s, br, 1H, N$\underline{H}$], 2.2–2.0[m, Me$_3$-$C_6H_2$, 18H] and 1.47[d, $^3J(HH)$ 7, CH$\underline{Me}$].

EXAMPLE 3

Preparation of 2-formyl(2-tert.butylanil),6-[(2-tert.butylphenyl)amino](methyl)methyl-pyridine 2c Compound 2c was prepared in analogous route to that outlined for 2a using $C_5H_3(CHN(2\text{-}t\text{-}Bu\text{-}C_6H_5))_2$ (5.0 g, 0.013 mol) as the starting 2,6-bis(imino)pyridine. Compound 2c was obtained analytically pure in good yield (3.64 g, 70%).

Mass spectrum m/z 413 [M$^+$].

EXAMPLE 4

Preparation of 2-acetyl(2,6-diisopropylylanil),6-[(2,6-diisopropylphenyl)amino](dimethyl)methyl-pyridine 2d Compound 2d was prepared in analogous route to that outlined for 2a using $C_5H_3(CMeN(2,6\text{-}i\text{-}Pr_2\text{-}C_6H_3))_2$ (5.0 g, 0.010 mol) as the starting 2,6-bis(imino)pyridine. Compound 2d was obtained analytically pure in good yield (3.61 g, 71%).

Mass spectrum m/z 497 [M$^+$].

Examples 1–4

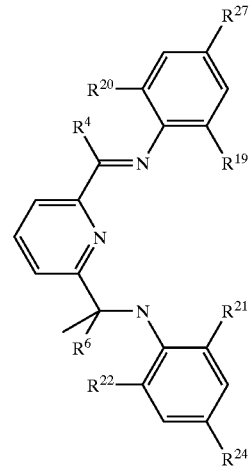

Example 1 (2a): $R^4$, $R^6$, $R^{24}$, $R^{27}$=H; $R^{19}$, $R^{20}$, $R^{21}$, $R^{22}$=i-Pr Example 2 (2b): $R^4$, $R^6$=H; $R^{19}$, $R^{20}$, $R^{21}$, $R^{22}$, $R^{24}$, $R^{27}$=Me Example 3 (2c): $R^4$, $R^6$, $R^{19}$, $R^{22}$, $R^{24}$, $R^{27}$, =H; $R^{20}$, $R^{21}$=t-Bu Example 4 (2d): $R^{24}$, $R^{27}$=H; $R^4$, $R^6$=Me; $R^{19}$, $R^{20}$, $R^{21}$, $R^{22}$=i-Pr Preparation of Complexes

EXAMPLE 5

Preparation of 2-formyl(2,6-diisopropylylanil),6-[(2,6-diisopropylphenyl)amino](methyl)methyl-pyridineFeCl$_2$ complex 3a FeCl$_2$ (0.20 g, 1.57 mmol) was dissolved in hot n-butanol (10 ml) at 80° C. A suspension of 2a (0.72 g, 1.62 mmol) in n-butanol was added dropwise at 80° C. The reaction mixture turned blue. After stirring at 80° C. for 15 minutes the reaction was allowed to cool to room temperature. The reaction volume was reduced to a few ml and diethylether added to preciptate the product as a blue powder, which was subsequently washed three times with diethylether (10 ml).

Yield: 0.76 g (83%). Mass spectrum: m/z 596 [M$^+$-Cl], 561 [M$^+$-2Cl]. Crystals of 3a suitable for a single crystal X-ray diffraction study were obtained by slow cooling of a hot acetonitrile solution of 3a.

EXAMPLE 6

Preparation of 2-formyl(2,4,6-trimethylanil),6-[(2,4,6-trimethylphenyl)amino](methyl)methyl-pyridineFeCl$_2$ complex 3b Complex 3b (0.46 g, 80%) was prepared by an analogous route to that outlined for 3a from FeCl$_2$ (0.15 g, 1.18 nmmol) and 2b (0.44 g, 1.18 mmol).

Mass spectrum: m/z 512 [M$^+$], 476 [M$^+$-Cl], 441 [M$^+$-2Cl].

EXAMPLE 7

Preparation of 2-formyl(2-tert.butylanil),6-[(2-tert.butylphenyl)amino](methyl)methyl-pyridineFeCl$_2$ complex 3c Complex 3c (0.37 g, 60%) was prepared by an analogous route to that outlined for 3a from FeCl$_2$ (0.15 g, 1.18 mmol) and 2c (0.47 g, 1.18 mmol).

Mass spectrum: m/z 540 [M$^+$], 504 [M$^+$-Cl], 469 [M$^+$-2Cl].

EXAMPLE 8

Preparation of 2-formyl(2,6-diisopropylylanil),6-[(2,6-diisopropylphenyl)amino](methylmethyl-pyridineFeBr$_2$ complex 3d Complex 3d (0.29 g, 61%) was prepared by an analogous route to that outlined for 3a from FeBr$_2$ (0.15 g, 0.695 mmol) and 2a (0.32 g, 0.695 mmol).

Mass spectrum: m/z 685 [M$^+$], 649 [M$^+$-Cl], 614 [M$^+$-2Cl].

EXAMPLE 9

Preparation of 2-acetyl(2,6-diisopropylylanil),6-[(2,6-diisopropylphenyl)amino](dimethyl)methyl-pyridineFeCl$_2$ complex 3e Complex 3e (0.46 g, 62%) was prepared by an analogous route to that outlined for 3a from FeCl$_2$ (0.15 g, 1.18 mmol) and 2d (0.59 g, 1.18 mmol).

Mass spectrum: m/z 540 [M$^+$], 504 [M$^+$-Cl], 469 [M$^+$-2Cl].

EXAMPLE 10

Preparation of 2-formyl(2,6-diisopropylylanil),6-[(2,6-diisopropylphenyl)amino](methyl)methyl-pyridineCoCl$_2$ complex 4

Complex 4 (0.48 g, 70%) was prepared by an analogous route to that outlined for 3a from CoCl$_2$ (0.15 g, 1.15 mmol) and 2a (0.54 g, 1.15 mmol).

Mass spectrum: m/z 599 [M$^+$], 563 [M$^+$-Cl], 528 [M$^+$-2Cl].

EXAMPLE 11

Preparation of 2-formyl(2,6-diisopropylylanil),6-[(2,6-diisopropylphenyl)amino](methyl)methyl-pyridineCrCl$_2$ complex 5

Complex 5 (0.42 g, 59%) was prepared by an analogous route to that outlined for 3a from CrCl$_2$ (0.15 g, 1.22 mmol) and 2a (0.57 g, 1.22 mmol).

Mass spectrum: m/z 592 [M$^+$], 557 [M$^+$-Cl], 521 [M$^+$-2Cl]. Crystals of 5 suitable for a single crystal X-ray diffraction study were obtained by slow cooling of a hot acetonitrile solution of 5.

EXAMPLE 12

Preparation of 2-formyl(2,6-diisopropylylanil),6-[(2,6-diisopropylphenyl)amino](methyl)methyl-pyridineZr(NMe$_2$)$_3$ complex 6

Compound 2a (1.003 g, 2.14 mmol) was dissolved in toluene (20 ml) and added dropwise to a toluene (20 ml) solution of Zr(NMe$_2$)$_4$ (0.571 g, 2.14 mmol). The solution immediately became orange in colour. The solution was then heated at 70° C. overnight. On cooling to room temperature the toluene was removed and heptane (60 ml) introduced. The solution was concentrated to half volume and left in the freezer to give small yellow crystals of 6 after several hours which were subsequently decanted and collected (0.89 g, 60%).

Mass spectrum: m/z 647 [M$^+$-NMe2].

EXAMPLE 13

Preparation of 2-acetyl(2.4-dimethylanil),6-[(2,4-dimethylphenyl)amido](n-butyl)methyl-pyridine FeCl complex 7

The 2,6-bis(imino)pyridine, C$_5$H$_3$(CMeN(2,4-Me$_2$-C$_6$H$_3$))$_2$ (0.994g, 2.69 mmol) was dissolved in tetrahydrofuran (30 ml) and cooled to −78° C. in an acetone/solid CO$_2$ cold bath. A solution of nBuLi (1.6 m in hexanes, Aldrich, 1.85cm$^3$, 2.96 mmol) was added dropwise to the 2,6-bis(imino)pyridine solution and stirred for 60 minutes. The reaction mixture was removed from the cold bath and stirred for a further 4 hours. The resultant purple solution was cooled to -78° C., with an acetone/solid CO$_2$ cold bath, and a suspension of FeCl$_2$ (0.341 g, 2.69 mmol, Aldrich) in tetrahydrofuran (20cm$^3$) added dropwise. After 20 minutes the reaction was removed from the cold bath and stirred at room temperature overnight. The volatile components of the reaction mixture were then removed in vacuo, giving a dark blue solid, and extracted into toluene (100 cm$^3$). The resultant soluble reaction fraction was isolated by filtration and dried in vacuo to give a dark blue, highly air sensitive, solid in good yield (0.87g, 62%)

EXAMPLE 14

Preparation of 2-acetyl(2,4,6-trimethylanil),6-[(2.4.6-trimethylphenyl)amido](n-butyl)methyl-pyridine VCl$_2$ complex 8

The 2,6-bis(imino)pyridine, C$_5$H$_3$(CMeN(2,4,6-Me$_3$-C$_6$H$_3$))$_2$(0.734g, 1.847 mmol) was dissolved in tetrahydrofuran (100 ml) and cooled to −78° C. in an acetone/solid CO$_2$ cold bath. A solution of nBuLi (1.6 m in hexanes, Aldrich, 1,27 cm$^3$, 2.03 mmol) was added dropwise to the 2,6-bis(imino)pyridine solution and stirred for 20 minutes. The reaction mixture was removed from the cold bath and stirred for a further 4 hours. The resultant purple solution was cooled to −78° C., with an acetone/solid CO$_2$ cold bath, and a solution of VCl$_3$(THF)$_3$ (0.69g, 1.847 mmol, Aldrich) in tetrahydrofuran (30cm$^3$) added dropwise, After 20 minutes the reaction was removed from the cold bath and stirred at room temperature overnight. The volatile components of the reaction mixture were then removed in vacuo, to give a green solid. The resultant solid was extracted into n-hexane (250cm$^3$), filtered and the volatile components of the solution removed in vacuo to give a green solid. (0.17 g, 16%).

EXAMPLE 15

Preparation of 2-acetyl(2.4-dimethylanil),6-[(2,4-dimethylphenyl)amido](n-butyl)methyl-pyridine TiCl$_2$ complex 9

The 2,6-bis(imino)pyridine, C$_5$H$_3$(CMeN(2,4-Me$_2$-C$_6$H$_3$))$_2$ (1.11 g, 2.79 mmol) was dissolved in tetrahydrofuran (30 ml) and cooled to −78° C. in an acetone/solid CO$_2$ cold bath. A solution of nBuLi (1.6 m in hexanes, Aldrich, 1.75cm$^3$, 2.79 mmol) was added dropwise to the 2,6-bis (imino)pyridine solution and stirred for 60 minutes. The reaction mixture was removed from the cold bath and stirred for a further 4 hours. The resultant purple solution was cooled to −78° C., with an acetone/solid $CO_2$ cold bath, and a suspension of $TiCl_3(THF)_3$ (1.035 g, 2.79 mmol, Aldrich) in tetrahydrofuran (20cm³) added dropwise. After 20 minutes the reaction was removed from the cold bath and stirred at room temperature overnight. The volatile components of the reaction mixture were then removed in vacuo and the reaction product extracted into toluene (100 cm³). The resultant soluble reaction fraction was isolated by filtration and dried in vacuo to give a dark green solid in good yield (1.28 g, 80%)

Polymerisations

The reagents used in the polymerisation tests were Ethylene Grade 3.5 (supplied from BOC), triisobutylaluminium (1M in toluene, supplied by Aldrich), and MAO (10% wt solution in toluene, supplied by Aldrich).

EXAMPLE 16

Schlenk Tube Polymerisation

The complexes 3–5 and 7–9 made in Examples 5 to 11 and 13 to 15 above were dissolved or suspended in toluene (40 ml) and the cocatalyst (methylaluminoxane, MAO – a 1.78M solution in toluene or for Example 16.10 $MeAlCl_2$, a 1.0M solution in hexanes) introduced. The tube was purged with ethylene and the contents stirred under 1 bar ethylene at 25° C. for the duration of the polymerization. After one hour the polymerization was terminated by the addition of aqueous hydrogen chloride. The solid produced was filtered off, washed with methanol and dried. The reaction mixture filtrate was separated and the hydrocarbon soluable fraction dried over anhydrous magnesium sulphate, filtered and the volatile components removed in vacuo.

TABLE 1

Schlenk test ethylene polymerisation runs using complexes 3–5 and 7–9

| EX. | Catalyst | (mmol) | MAO mmol/equiv | Run time mins | Pressure $C_2H_4$/bar | Yield PE/g | Activity g/mmol/h/bar |
|---|---|---|---|---|---|---|---|
| 16.1 | 3a | (0.02) | 8/400 | | 1 | 0.40 | 20 |
| 16.2 | 3b | (0.02) | 8/400 | | 1 | 0.36 | 18 |
| 16.3 | 3c | (0.02) | 8/400 | | 1 | 0.25 | 12 |
| 16.4 | 3d | (0.02) | 8/400 | | 1 | 0.05 | 3 |
| 16.5 | 3e | (0.02) | 8/400 | | 1 | 2.10 | 90 |
| 16.6 | 4 | (0.02) | 8/400 | | 1 | 0.03 | 2 |
| 16.7 | 5 | (0.02) | 8/400 | | 1 | 0.15 | 8 |

TABLE 1-continued

Schlenk test ethylene polymerisation runs using complexes 3–5 and 7–9

| EX. | Catalyst | (mmol) | MAO mmol/equiv | Run time mins | Pressure $C_2H_4$/bar | Yield PE/g | Activity g/mmol/h/bar |
|---|---|---|---|---|---|---|---|
| 16.8 | 7 | (5.2) | 2/100 | 40 | 1 | 0.87* | 112 |
| 16.9 | 8 | (7.8) | 1.78/230 | 15 | 1 | 1.62 | 830 |
| 16.10 | 8 | (9.0) | 1.6/180# | 30 | 1 | 0.38 | 85 |
| 16.11 | 9 | (5.2) | 3.6/680 | 60 | 1 | 1.55 | 300 |

*liquid yield
activator $MeAlCl_2$

EXAMPLE 17

High Pressure Polymerisation

Examples 17.1–17.5

A 1 liter reactor was baked out under a nitrogen flow for at least 1 hour at >85° C. The reactor was then cooled to 35 or 50° C. Isobutane (0.5 liter) and triisobutylaluminium (TIBA) were then added and the reactor boxed in nitrogen. The TIBA was allowed to scavenge for poison in the reactor for at least 1 hour. Ethylene was introduced into the reactor until a pre-determined over-pressure was achieved. The catalyst solution in toluene [in the case of the complex 6 initial activation with trimethylaluminium (TMA) (0.05 ml, 0.1 mmol) was followed by addition of MAO] was then injected under nitrogen. The reactor pressure was maintained constant throughout the polymerisation run by computer controlled addition of additional ethylene. The polymerisation time was 1 hour. Upon termination of the run the reactor contents were isolated, washed with aqueous HCl, methanol and dried in a vacuum oven at 50° C.

Examples 17.6–17.7

A 1 liter reactor was baked out under a nitrogen flow for at least 1 hour at >85° C. The reactor was then cooled to 35 or 50° C. Isobutane (0.5 liter) and MAO were then added and the reactor boxed in nitrogen. The MAO was allowed to scavenge for poison in the reactor for at least 1 hour. Ethylene was introduced into the reactor until a pre-determined over-pressure was achieved. The catalyst solution in toluene (a toluene solution was prepared to which was added MAO) was then injected under nitrogen. The reactor pressure was maintained constant throughout the polymerisation run by computer controlled addition of additional ethylene. The polymerisation time was 1 hour. Upon termination of the run the reactor contents were isolated, washed with aqueous HCl, methanol and dried in a vacuum oven at 50° C.

TABLE 2a

High pressure ethylene polymerisation runs using complexes 3 and 6

| EX. | Catalyst (mmol) | Activator (mmol/equiv) | TIBA ml | Temp ° C. | Pressure $C_2H_4$/bar | Yield PE/g | Activity g/mmol/h/bar |
|---|---|---|---|---|---|---|---|
| 17.1 | 3a (0.025) | MAO (10/400) | 2 | 35 | 10 | 5.2 | 21 |
| 17.2 | 3b (0.027) | MAO (10.8/400) | 2 | 35 | 10 | 3.7 | 14 |
| 17.3 | 3b (0.025) | MAO (8/400) | 2 | 50 | 10 | 1.9 | 7 |
| 17.4 | 3e (0.025) | MAO (8/400) | 2 | 35 | 10 | 27.8* | 110 |
| 17.5 | 6 (0.020) | TMA/MAO (8/400) | 2* | 50 | 10 | 8.9 | 45 |

*GPC data: $M_w$ 896 000; $M_n$ 161 000; $M_w/M_n$ 5.5; $M_{pk}$ 388 000

TABLE 2b

High pressure ethylene polymerisation runs using complex 9

| EX. | Catalyst (mmol) | Activator (mmol/equiv) | MAO ml | Temp °C. | Pressure $C_2H_4$/bar | Yield PE/g | Activity g/mmol/h/bar |
|---|---|---|---|---|---|---|---|
| 17.6 | 9 (0.0009) | MAO (0.356/400) | 3 | 50 | 10 | 0.83 | 92 |
| 17.7 | 9 (0.009) | MAO (10.8/400) | 3 | 40 | 10* | 12.9 | 150 |

*50 mls 1-hexene added to reactor

13C NMR data Ex. 17.6: 1.7 vinyl groups per 1000C, 0.6 ethyl branches per 1000C, 0.1>C6 branches.

13C NMR data Ex 17.7: 2.0 vinyl groups per 1000C, 2.1 ethyl branches per 1000C, 4.0 butyl branches per 1000C.

Oxygen-containing Complexes

EXAMPLE 18

Preparation of 2-acetyl(2,6-diisopropylylanil),6-acetyl-pyridine 10

2,6-diacetylpyridine, (2.0 g, 0.012 mol) was dissolved in ethanol (40 ml) and one equivalent of 2,6-diisopropylaniline (2.31 ml, 0.022 mol) introduced followed by two drops of acetic acid. The reaction mixture was stirred at reflux overnight. The solvent was taken to dryness and adsorbed onto silica and loaded onto the top of a chromatography column. Elution with mixtures of hexane:ether gave 10 in moderate yield (1.38 g, 35%).

Compound 10: Mass spectrum: m/z 322 [M$^+$]. $^1$H NMR (CDCl$_3$): d 8.58 [d, $^3$J(HH) 8, 1H, Py-H], 8.14 [d, $^3$J(HH) 8, Py-H], 7.95 [tr, 1H, Py-H], 7.2–7.0 [m, 3H, Ar], 2.81 [s, 3H, CMeO], 2.75 [sept, $^3$J(HH) 7, 2H, CHMe$_2$], 2.29 [s, 3H, CMeNAr], 1.17 [d, 6H, CHMe$_2$] and 1.16 [d, 6H, CHMe$_2$].

EXAMPLE 19

Preparation of 2-acetyl(2,6-diisopropylylanil),6-(dimethyl)methanol-pyridine 11

Compound 11 was prepared in a two-step procedure:

Firstly, 10 (0.60 g, 0.0019 mol) was treated with two equivalents of trimethylalumninium (TMA) (1.86 ml, 2.0 M in Toluene, 0.0037 mol) in toluene (20 ml) and refluxed overnight. The toluene was then stripped off and the intermediate recrystallised from hot acetonitrile (30 ml). Yellow crystals of the intermediate were obtained in 79% (1.14 g) yield.

The intermediate (1.14 g, 0.0024 mol) was then suspended in pentane (30 ml), and water slowly added over a period of 0.5 h and the reaction mixture left to stir for a further 2 h. The pentane was stripped off and chloroform (30 ml) introduced. The aluminium salts were then filtered off and the pale yellow solution taken to dryness to give 11 (0.75 g, 91%).

Compound 11: Mass spectrum m/z 338 [M$^+$]. $^1$H NMR (CDCl$_3$): d 8.30 [d, $^3$J(HH) 8, 1H, Py-H], 7.84 [tr, 1H, Py-H], 7.49[d, 1H, Py-H], 7.2–7.0 [m, 3H, (CHMe$_2$)$_2$-C$_6$H$_3$], 5.24 [s, br, 1H, C Me$_2$OH], 2.70 [sept, $^3$J(HH) 7, 2H, CH Me$_2$], 2.23 [s, br, 3H, CAMe], 1.61 [s, 6H, C Me$_2$OH] and 1.15 [d, 12H, CH Me$_2$].

EXAMPLE 19

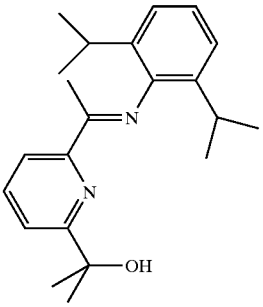

EXAMPLE 20

Preparation of 2-acetyl(2,6-diisopropylylanil),6-(dimethyl)methanol-pyridineFeCl$_2$ complex 12

FeCl$_2$ (0.15 g, 1.18 mmol) was dissolved in hot n-butanol (10 ml) at 80° C. A suspension of 12 (0.40g, 1.18 mmol) in n-butanol was added dropwise at 80° C. The reaction mixture turned blue. After stirring at 80° C. for 15 minutes the reaction was allowed to cool to room temperature. The reaction volume was reduced to a few ml and diethylether added to precipitate the product as a blue powder, which was subsequently washed three times with diethylether (10 ml).

Yield: 0.45 g (83%). Mass spectrum: m/z 465 [M$^+$], 430 [M$^+$-Cl], 561 [M$^+$-2Cl].

EXAMPLE 21

Preparation of 2-acetyl(2,6-diisopropylylanil),6-(dimethyl)methanol-pyridineCoCl$_2$ complex 13

Complex 13 (0.44 g, 80%) was prepared by an analogous route to that outlined for 12 but from CoCl$_2$ (0.15 g, 1.18 mmol) and 11 (0.40 g, 1.18 mmol).

Mass spectrum: m/z 433 [M$^+$-Cl], 397 [M$^+$-2Cl].

Polymerisations

The reagents used in the polymerisation tests were Ethylene Grade 3.5 (supplied from BOC), and MAO (10% wt solution in toluene, supplied by Aldrich).

EXAMPLE 22

Schlenk Tube Polymerisation

The complexes 12 and 13 made in Examples 20 and 21 above (0.02 mmol) were dissolved or suspended in toluene (40 ml) and the cocatalyst (methylaluminoxane, MAO –8.0 mmol, 400 equiv.) introduced. The tube was purged with ethylene and the contents stirred under 1 bar ethylene for the duration of the polymerization. After one hour the polymerization was terminated by the addition of aqueous hydrogen chloride. The solid produced was filtered off, washed with methanol and dried.

TABLE 3

Schlenk test ethylene polymerisation runs using complexes 12 and 13

| EX. | Catalyst (mmol) | Activator (mmol/equiv) | Temp ° C. | Pressure $C_2H_4$/ bar | Yield PE/g | Activity g/mmol/ h/bar |
|---|---|---|---|---|---|---|
| 22.1 | 12 (0.02) | MAO (2/100) | 25 | 1 | 0.90 | 45 |
| 22.2 | 13 (0.02) | MAO (2/100) | 25 | 1 | 0.02 | 1 |

EXAMPLE 23

Preparation of 2-acetyl(2,4,6-trimethylanil),6-[(2,4,6-trimethylphenyl)amido](n-butylmethyl-pyridine FeCl complex 14

The 2,6-bis(imino)pyridine, $C_5H_3(CMeN(2,4,6-Me_3-C_6H_3))_2$ (0.7g, 1.76 mmol) was dissolved in tetrahydrofuran (10 ml) and cooled to −78° C. in an acetone/solid $CO_2$ cold bath. A solution of nBuLi (1.6 m in hexanes, Aldrich, 1.21 cm³, 1.938 mmol) was added dropwise to the 2,6-bis(imino) pyridine solution and stirred for 60 minutes. The reaction mixture was removed from the cold bath and stirred for a further 4 hours. The resultant purple solution was cooled to −78° C., with an acetone/solid $CO_2$ cold bath, and a suspension of $FeCl_2$ (0.223g, 1.76 mmol, Aldrich) in tetrahydrofuran (20 cm³) added dropwise. After 20 minutes the reaction was removed from the cold bath and stirred at room temperature overnight. The volatile components of the reaction mixture were then removed in vacuo, giving a dark blue solid, and extracted into pentane (150 cm³). The resultant soluble reaction fraction was isolated by filtration and dried in vacuo to give a dark blue, highly air sensitive, solid in good yield (0.7 g, 73%)

EXAMPLE 24

Preparation of 2-acetyl(2,4,6-trimethylanil),6-[(2,4,6-trimethylphenylamidol(n-butyl)methyl-pyridine CoCl complex 15

The 2,6-bis(imino)pyridine, $C_5H_3(CMeN(2,4,6-Me_3-C_6H_3))_2$(3 g, 7.56 mmol) was dissolved in tetrahydrofuran (100 ml) and cooled to −78° C. in an acetone/solid $CO_2$ cold bath. A solution of nBuLi (1.6 m in hexanes, Aldrich, 5.19 cm³, 8.31 mmol) was added dropwise to the 2,6-bis(imino) pyridine solution and stirred for 20 minutes. The reaction mixture was removed from the cold bath and stirred for a further 4 hours. The resultant purple solution was cooled to −78° C., with an acetone/solid $CO_2$ cold bath, and a suspension of $CoCl_2$ (0.981 g, 7.56 mmol, Aldrich) in tetrahydrofuran (30 cm³) added dropwise. After 20 minutes the reaction was removed from the cold bath and stirred at room temperature overnight. The volatile components of the reaction mixture were then removed in vacuo, to give a dark brown solid, and extracted into a pentane (50 cm³) and toluene (100 cm³) mix. The resultant soluble reaction fraction was isolated by filtration and dried iln vacuo to give a dark red solid. (0.79 g, 19%).

EXAMPLE 25

Preparation of 14 supported on MAO/silica

Methyl aluminoxane (24 ml of 1.78M in toluene, supplied by Witco) was added to silica (5 g of grade ES70X supplied by Crosfield) which had been heated under flowing nitrogen at 250° C. The silica/MAO was heated at 80° C. for 1 hour before being washed toluene (5×10 ml aliquots) and dried in vacuo. Complex 14 (42 mg) and silica/MAO (1 g) were slurried in toluene (20 ml) and then heated at 70° C. for 60 minutes. The reaction mixture was cooled to room temperature and agitated occasionally over a 24 hour period. The volatile components of the reaction mixture were then removed under reduced pressure at room temperature to give a blue solid.

EXAMPLE 26

Polymerisations

General: The reagents used in the polymerisation tests were Ethylene Grade 3.5 (supplied from BOC), triisobutylalurninium (1M in toluene, supplied by Aldrich), 1-hexene (redistilled over sodium metal, supplied by Aldrich) and methylaluminoxane (MAO) (10% wt solution in toluene, supplied by Witco).
(i) Slurry tests The result of the high pressure tests are shown in Table 1. A 1 liter reactor was baked out under a nitrogen flow for at least 1 hour at >85° C. The reactor was then cooled to 50° C. Isobutane (0.5 liter) and triisobutylaluminium were then added and the reactor boxed in nitrogen. The alkyl aluminium was allowed to scavenge for poisons in the reactor for at least 1 hour. Ethylene was introduced into the reactor until a predetermined over-pressure was achieved. The catalyst solution† in toluene was then injected under nitrogen. The reactor pressure was maintained constant throughout the polymerisation run by computer-controlled addition of additional ethylene. The polymerisation time was 1 hour. Upon termination of the run the reactor contents were isolated, washed with aqueous HCl, methanol and dried in a vacuum oven at 40° C.

TABLE 4

Results of high pressure ethylene polymerisation runs using procatalysts 14 and 15

| Run | Procatalyst ($10^{-7}$ mol) | MAO mmol/equiv | Al(iBu)$_3$ ml | T ° C. | pC$_2$H$_4$ bar | Yield PE g | Activity g mmol$^{-1}$ h$^{-1}$ bar$^{-1}$ |
|---|---|---|---|---|---|---|---|
| 1* | 14 (6.41) | 0.55/860 | 3 | 50 | 7.9 | 39 | 7630 |
| 2 | 15 (55.83) | 5.58/1000 | 3 | 50 | 7.9 | 35 | 800 |

*Carried out over a period of 60 min.
*GPC data: M$_w$ 629000; M$_n$ 19000; M$_w$/M$_n$ 32.8; M$_{pk}$ 62000

(ii) Gas Phase Test

A 3 liter reactor was baked out under flowing nitrogen for least 1 hour at 78° C. before being cooled to 30° C. Sodium chloride charge powder (300 g) having an average particle diameter of less than 1 mm and having been pre-dried under vacuum at 160° C. for more than 4 hours was added, followed by trimethyl aluminium (3 ml, 2M in hexanes, supplied by Aldrich). The reactor was then closed and heated to 78° C. The alkyl aluminium was allowed to scavenge any poisons present in the reactor for 90 minutes. The reactor was then purged four times, by pressurising to 4 bar with nitrogen and then venting. 1-hexene was added to the reactor to give 0.02 bar pressure followed by ethylene (8 bar). The catalyst (0.30 g) as prepared above was injected under nitrogen and the temperature then adjusted to 80° C. The polymerisation was allowed to continue for 90 minutes before being terminated by purging the ethylene from the reactor using nitrogen, and reducing the temperature to below 30° C. The polymer was washed with water to remove the sodium chloride, then with acidified methanol (50 ml HCl/2.5 liters methanol) and finally with water/ethanol (4:1 v/v). The polymer was dried under vacuum, at 40° C., for 16 hours. 39.68 g of dried polymer was produced.

13C NMR: 0.2 butyl branches per 1000C GPC data: $M_w$ 481000; $M_n$ 48000; $M_w/M_n$ 9.9; $M_{pk}$ 120000

EXAMPLE 27

Preparation of MAO on Silica

Toluene (200 ml) was added to a vessel containing silica (ES70X grade, calcined at 200° C. overnight, 20.5 g after calcination) under an inert atmosphere. The slurry was mechanically stirred and MAO (1.5M, 62.1 mmol, 41.4 ml) was added via syringe. The mixture was stirred for 1 hour at 80° C. before removing excess toluene and drying under vacuum to obtain 15% w/w MAO on silica in quantitative yield.

EXAMPLE 28

Ethylene Homopolymerisation Using as Catalyst Complex 8 Supported on MAO/silica

The reactor (1L) was heated under flowing nitrogen for 1 hour at 80° C. before being cooled to 30° C. Tri-isobutyl aluminium scavenger (3 ml, 1M in toluene, 3 mmol), and isobutane (500 ml) were added. The reactor was closed and heated to 80° C., ethylene was admitted such that the total pressure was increased by 8 bar. In a separate vessel, precatalyst 8 (10 mmol) was mixed with MAO/ES70X silica (0.33 g, prepared as described in Example 27 above, 15% w/w MAO on silica) and toluene (10 mL) was added. The mixture was shaken thoroughly and the catalyst particles were allowed to settle forming a blue coloured solid beneath the colourless toluene supernatant. The catalyst was shaken again to form a slurry with the mixture injected directly into the reactor. The reaction was allowed to proceed for 60 minutes before terminating by shutting off the ethylene supply and venting the reactor pressure. 28.5 g of polymer was recovered after drying the reactor contents overnight at 40° C. under reduced pressure.

What is claimed is:

1. A complex having the Formula A

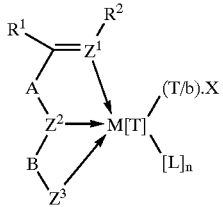

(Formula A)

wherein M is a transition metal, lanthanide or actinide; X represents an atom or group covalently or ionically bonded to the transition metal M; b is the valency of the atom or group X; $Z^1$ is N or P; $Z^2$ is N, P, $N^-$, $P^-$ or $NR^5$; $Z^3$ is one of N, P, O, S, $NHR^3$, $NR^3R^4$, OH, $OR^3$, SH, $SR^3$, $PHR^3$, $PR^3R^4$, $(NR^3)^-$, $O^-$, $S^-$, $(PR^3)^-$, $P(R^3R^4)O$, $NR^3$ or $PR^3$, subject to the proviso that the ligand joined to M via $Z^1$, $Z^2$ and $Z^3$ is monoanionic or neutral, and that when neutral the ligand is not a pyridyl diimine ligand; T is the oxidation state of the transition metal M when the ligand is neutral, and is one less than the oxidation state of M when the ligand is monoanionic; A and B are independently hydrocarbyl, substituted hydrocarbyl, heterohydrocarbyl or substituted heterohydrocarbyl, and may together with $Z^2$ form part of a heterocyclic substituent; B may be joined to $Z^3$ by either a single or a double bond; $R^1$ to $R^5$ are each independently selected from the group consisting of hydrogen, halogen, hydrocarbyl, substituted hydrocarbyl, heterohydrocarbyl and substituted heterohydrocarbyl, and any two or more of $R^1$ to $R^5$ when hydrocarbyl may be joined together to form a ring; L is a solvate molecule, and n is from 0 to 5.

2. The complex according to claim 1, wherein M is Ti[II], Ti[III], Ti[IV], Fe[II], Fe[III], Co[II], Co[III], Ni[II], Cr[II], Cr[III], Mn[II], Mn[III], Mn[IV], Ta[II], Ta[III], Ta[IV], Rh[II], Rh[III], Y[II], Y[III], Sc[II], Sc[III], Ru[II], Ru[III], Ru[IV], Pd[II], Zr[II], Zr[III], Zr[IV], Hf[II], Hf[III], Hf[IV], V[II], V[III], V[IV], Nb[II], Nb[III], Nb[IV] or Nb[V].

3. A complex having the following formula

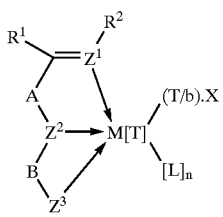

wherein M is Ti[II], Ti[III], Ti[IV], Fe[II], Fe[III], Co[II], Co[III], Ni[II], Cr[II], Cr[III], Mn[II], Mn[III], Mn[IV], Ru[II], Ru[III], Ru[IV], Pd[II], Zr[II], Zr[III], Zr[IV], Hf[II], Hf[III], Hf[IV], V[II], V[III], V[IV], Nb[II], Nb[III], or Nb[IV]; X represents an atom or group covalently or ionically bonded to the transition metal M; b is the valency of the atom or group X; $Z^1$ is N or P; $Z^2$ is N, P, $N^-$, $P^-$ or $NR^5$; $Z^3$ is one of N, P, O, S, $NHR^3$, $NR^3R^4$, OH, $OR^3$, SH, $SR^3$, $PHR^3$, $PR^3R^4$, $(NR^3)^-$, $O^-$, $S^-$, $(PR^3)^-$, $P(R^3R^4)O$, $NR^3$ or $PR^3$, subject to the proviso that one of $Z^2$ and $Z^3$ is anionic; T is one less than the oxidation state of M; A and B are independently hydrocarbyl, substituted hydrocarbyl, heterohydrocarbyl or substituted heterohydrocarbyl, and may together with $Z^2$ form part of a heterocyclic substituent; B may be joined to $Z^3$ by either a single or a double bond; $R^1$ to $R^5$ are each independently selected from the group consisting of hydrogen, halogen, hydrocarbyl, substituted hydrocarbyl, heterohydrocarbyl, and substituted heterohydrocarbyl, and any two or more of $R^1$ to $R^5$ when hydrocarbyl may be joined together to form a ring; L is a solvate molecule, and n is from 0 to 5.

4. The complex according to claim 1 or 3, wherein either $Z^2$ or $Z^3$ is $N^-$ and is joined to M by a covalent bond.

5. A complex having the following formula

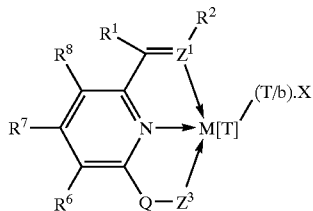

wherein M is Ti(II), Ti(III), Ti(IV), Fe[II], Fe[III], Co[I], Co[II], Co[III], Ni(I), Ni(II), Cr(II), Cr(III), Mn[I], Mn[II], Mn[III], Mn[IV], Ru[II], Ru[III], Ru[IV], Pd(I), Pd(II), Zr(II), Zr(III), Zr(IV), Hf(II), Hf(III) or Hf(IV); X represents an atom or group covalently or ionically bonded to the transition metal M; b is the valency of the atom or group X; $Z^3$ is one of $NHR^3$, $NR^3R^4$, OH, $OR^3$, SH, $SR^3$, $PHR^3$, $PR^3R^4$, $(NR^3)^-$, $O^-$, $S^-$, $(PR^3)^-$ or $P(R^3R^4)O$; T is the oxidation state of the transition metal M when $Z^3$ is neutral, and is one less than the oxidation state of M when $Z^3$ is anionic; $Z^1$ is N or P; Q is joined to $Z^3$ by a single bond and is hydrocarbyl, substituted hydrocarbyl, heterohydrocarbyl or substituted heterohydrocarbyl; $R^1$–$R^4$ and $R^6$ to $R^8$ are independently selected from the group consisting of hydrogen, halogen, hydrocarbyl, substituted hydrocarbyl, heterohydrocarbyl, and substituted heterohydrocarbyl; and when any two or more of $R^1$–$R^4$ and $R^6$–$R^8$ are hydrocarbyl, substituted hydrocarbyl, heterohydrocarbyl or substituted heterohydrocarbyl, said two or more of $R^1$–$R^4$ and $R^6$–$R^8$ can be linked to form one or more cyclic substituents.

6. The complex of claim 5, wherein Q is —$C(R^9)(R^{10})$ and $R^9$ to $R^{10}$ are independently selected from the group consisting of hydrogen, halogen, hydrocarbyl, substituted hydrocarbyl, heterohydrocarbyl, and substituted heterohydrocarbyl; and when any two or more of $R^1$–$R^4$ and $R^6$–$R^{10}$ are hydrocarbyl, substituted hydrocarbyl, heterohydrocarbyl or substituted heterohydrocarbyl, said two or more of $R^1$–$R^4$ and $R^6$–$R^{10}$ can be linked to form one or more cyclic substituents.

7. The complex according to claim 1, which comprises the skeletal unit of Formula B (Formula B)

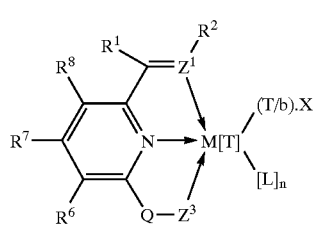

wherein M is Ti[II], Ti[III], Ti[IV], Fe[II], Fe[III], Co[II], Co[III], Ni[II], Cr[II], Cr[III], Mn[II], Mn[III], Mn[IV], Ru[II], Ru[III], Ru[IV], Pd[II], Zr[II], Zr[III], Zr[IV], Hf[II], Hf[III], Hf[IV], V[II], V[III], V[IV], Nb[II], Nb[III], or Nb[IV]; X represents an atom or group covalently or ionically bonded to the transition metal M; b is the valency of the atom or group X; $Z^1$ is N or P; $Z^3$ is one of $NHR^3$, $NR^3R^4$, OH, $OR^3$, SH, $SR^3$, $PHR^3$, $PR^3R^4$, $(NR^3)^-$, $O^-$, $S^-$, $(PR^3)^-$ or $P(R^3R^4)O$; T is the oxidation state of the transition metal M when $Z^3$ is neutral, and is one less than the oxidation state of M when $Z^3$ is anionic; Q is joined to $Z^3$ by a single bond and is hydrocarbyl, substituted hydrocarbyl, heterohydrocarbyl or substituted heterohydrocarbyl; $R^1$–$R^4$ and $R^6$–$R^8$ are each independently selected from the group consisting of hydrogen, halogen, hydrocarbyl, substituted hydrocarbyl, heterohydrocarbyl, and substituted heterohydrocarbyl, and when hydrocarbyl any two or more of $R^1$–$R^4$ and $R^6$–$R^8$ may be joined together to form a ring; L is a solvate molecule, and n is from 0 to 5.

8. The complex according to claim 3, which comprises the skeletal unit of Formula B (Formula B)

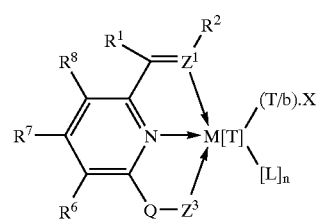

wherein M is Ti[II], Ti[III], Ti[IV], Fe[II], Fe[III], Co[II], Co[III], Ni[II], Cr[II], Cr[III], Mn[II], Mn[III], Mn[IV], Ru[II], Ru[III], Ru[IV], Pd[II], Zr[II], Zr[III], Zr[IV], Hf[II], Hf[III], Hf[IV], V[II], V[III], V[IV], Nb[II], Nb[III], or Nb[IV]; X represents an atom or group covalently or ionically bonded to the transition metal M; b is the valency of the atom or group X; $Z^1$ is N or P; $Z^3$ is one of $(NR^3)^-$, $O^-$, $S^-$, or $(PR^3)^-$; T is one less than the oxidation state of M; Q is joined to $Z^3$ by a single bond and is hydrocarbyl, substituted hydrocarbyl, heterohydrocarbyl or substituted heterohydrocarbyl; $R^1$–$R^3$ and $R^6$–$R^8$ are each independently selected from the group consisting of hydrogen, halogen, hydrocarbyl, substituted hydrocarbyl, heterohydrocarbyl, and substituted heterohydrocarbyl, and when hydrocarbyl any two or more of $R^1$–$R^3$ and $R^6$–$R^8$ may be joined together to form a ring; L is a solvate molecule, and n is from 0 to 5.

9. The complex of claim 7 or 8, wherein Q is —$C(R^9)(R^{10})$ and $R^9$ to $R^{10}$ are independently selected from the group consisting of hydrogen, halogen, hydrocarbyl, substituted hydrocarbyl, heterohydrocarbyl, and substituted heterohydrocarbyl; and when any two or more of $R^1$–$R^4$ and $R^6$–$R^{10}$ are hydrocarbyl, substituted hydrocarbyl, heterohydrocarbyl or substituted heterohydrocarbyl, said two or more of $R^1$–$R^4$ and $R^6$–$R^{10}$ can be linked to form one or more cyclic substituents.

10. The complex according to claim 7 or 8, wherein n is 0.

11. The complex according to claim 7 or 8, wherein $R^2$ is represented by the following structure

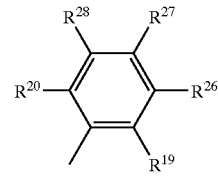

and R³ is represented by the following structure

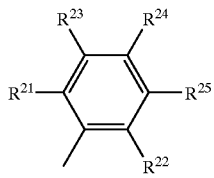

wherein R¹⁹ to R²⁸ are each independently selected from the group consisting of hydrogen, halogen, hydrocarbyl, substituted hydrocarbyl, heterohydrocarbyl, and substituted heterohydrocarbyl, and when hydrocarbyl any two or more of R¹⁹ to R²⁸ thereof may be joined together to form a ring.

12. The complex according to claim 7 or 8, wherein R² is represented by the following structure

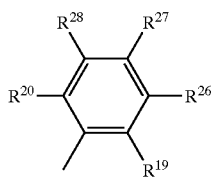

and R³ is represented by the following structure

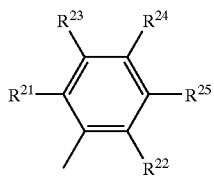

and R⁶ to R⁸ and R¹⁹ to R²⁸ are independently selected from the group consisting of hydrogen and $C_1$ to $C_8$ hydrocarbyl.

13. The complex of claim 12, wherein R⁶ to R⁸ and R¹⁹ to R²⁸ are independently selected from the group consisting of methyl, ethyl, n-propyl, iso-propyl, n-butyl, sec-butyl, tert.-butyl, n-pentyl, neopentyl, n-hexyl, 4-methylpentyl, n-octyl, phenyl, and benzyl.

14. The complex according to claim 12, wherein R²⁴ and R²⁷ contain at least two carbon atoms.

15. The complex according to claim 12, wherein R¹⁹, R²⁰, R²¹ and R²² are each independently selected from the group consisting of methyl, ethyl, n-propyl, iso-propyl, n-butyl, sec-butyl, tert.-butyl, n-pentyl, neopentyl, n-hexyl, 4-methylpentyl, n-octyl, phenyl, and benzyl.

16. The complex according to claim 1, wherein R¹ to R⁵ are each independently 2,4,6-trimethylphenyl, 2,6-diisopropylphenyl, 2,6-dimethyl-4-tert.butyl-phenyl, 2,6-dimethylphenyl, 2-methylphenyl, 2,4-dimethylphenyl, 2,3-dimethylphenyl, 2-ethylphenyl, 2-isopropylphenyl, or 2-tert.butyl.

17. The complex according to claim 1, wherein Z¹ is N, and Z³ is (NR³)⁻ or O⁻.

18. The complex according to claim 7 or 8, wherein L is selected from the group consisting of tetrahydrofuran, diethylether, ethanol, butanol, a primary secondary or tertiary amine, and a phosphine.

19. The complex according to claim 7 or 8, wherein X is selected from the group consisting of halide, sulphate, nitrate, thiolate, thiocarboxylate, $BF_4^-$, $PF_6^-$, hydride, hydrocarbyloxide, carboxylate, hydrocarbyl, substituted hydrocarbyl, heterohydrocarbyl, and β-diketonates.

20. The complex according to claim 7 or 8, wherein X is selected from the group consisting of chloride, bromide, methyl, ethyl, propyl, butyl, octyl, decyl, phenyl, benzyl, methoxide, ethoxide, isopropoxide, tosylate, triflate, formate, acetate, phenoxide, and benzoate.

21. The complex according to claim 7, which comprises:
2-formyl(2,6-diisopropylylanil),6-[(2,6-diisopropylphenyl)amino](methyl)methyl-pyridine.FeCl₂;
2-formyl(2,4,6-trimethylanil),6-[(2,4,6-trimethylphenyl)amino](methyl)methyl-pyridine.FeCl₂;
2-formyl(2-tert.butylanil),6-[2-tert.butylphenyl)amino](methyl)methyl-pyridine.FeCl₂;
2-formyl(2,6-diisopropylylanil),6-[(2,6-diisopropylphenyl)amino](methyl)methyl-pyridine.FeBr₂;
2-acetyl(2,6-diisopropylylanil),6-[(2,6-diisopropylphenyl)amino](dimethyl)methyl-pyridine.FeCl₂;
2-formyl(2,6-diisopropylylanil),6-diisopropylphenyl)amino](methyl)methyl-pyridine.CoCl₂;
2-formyl(2,6-diisopropylylanil),6-diisopropylphenyl)amino](methyl)methyl-pyridine.CrCl₂;
2-formyl(2,6-diisopropylylanil),6-diisopropylphenyl)amino](methyl)methyl-pyridine.Zr(NMe₂)₃;
2-acetyl(2,6-diisopropylylanil),6-(dimethyl)methanol-pyridine.FeCl₂;
2-acetyl(2,6-diisopropylylanil),6-(dimethyl)methanol-pyridineCoCl₂;
2-acetyl(2,4,6-trimethylanil),6-[(2,4,6-trimethylphenyl)amido]n-butyl)methyl-pyridine.FeCl; or
2-acetyl(2,4,6-trimethylanil),6-[(2,4,6-trimethylphenyl)amido]n-butyl)methyl-pyridine.CoCl.

22. A polymerisation catalyst comprising
(1) a complex according to claim 1, and
(2) an activating quantity of at least one activator compound.

23. The catalyst according to claim 22, wherein the activator is selected from the group consisting of organoaluminium compounds, hydrocarbylboron compounds and salts of a cationic oxidising agent and a non-coordinating compatible anion.

24. The catalyst according to claim 22, wherein the activator is selected from the group consisting of trimethylaluminium, triethylaluminium, tri-isobutylaluminium, tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes.

25. The catalyst according to claim 22, further comprising a neutral Lewis base.

26. The catalyst according to claim 25, wherein the neutral Lewis base is selected from the group consisting of alkenes (other than 1-olefins) or alkynes, primary, secondary and tertiary amines, amides, phosphoramides, phosphines, phosphites, ethers, thioethers, nitriles, esters, ketones, aldehydes, carbon monoxide and carbon dioxide, sulphoxides, sulphones and boroxines.

27. The catalyst according to claim 22, which is supported on a support material comprising silica, alumina, $MgCl_2$ or zirconia, or on a polymer or prepolymer comprising polyethylene, polypropylene, polystyrene, or poly (aminostyrene).

28. The catalyst according to claim 22, which comprises more than one complex (1), or a complex (1) plus a further tridentate nitrogen-containing Fe or Co complex.

29. The catalyst according claim 22, which comprises a complex (1) plus a further catalyst selected from the group consisting of a Ziegler-Natta catalyst system, metallocene-based catalysts, monocyclopentadienyl- or constrained geometry based catalysts, and heat activated supported chromium oxide catalysts.

30. A process for the polymerisation or copolymerisation of 1-olefins, comprising contacting a 1-olefin under polymerisation conditions with the complex or a catalyst containing the complex, according to claim 1.

31. A process for the polymerization or copolymerization of 1-olefins, comprising the steps of:
   a) preparing a prepolymer-based catalyst by contacting one or more 1-olefins with a catalyst, and
   b) contacting the prepolymer-based catalyst with one or more 1-olefins under polymerization conditions,
   wherein the catalyst is as defined in claim 22.

32. The process according to claim 30, wherein the polymerisation is conducted in the presence of hydrogen as a molecular weight modifier.

33. The process according to claim 30, wherein the polymerisation is conducted under solution phase, slurry phase or gas phase conditions.

34. The process according to claim 30, wherein the polymerisation is conducted under gas phase fluidised bed conditions.

35. The process according to claim 30, wherein the polymerisation is conducted under slurry phase conditions in an autoclave or continuous loop reactor.

36. The complex according to claim 13, wherein $R^{24}$ and $R^{27}$ contain at least two carbon atoms.

* * * * *

UNITED STATES PATENT AND TRADEMARK OFFICE
CERTIFICATE OF CORRECTION

PATENT NO.    : 6,683,141 B1  
DATED         : January 27, 2004  
INVENTOR(S)   : Vernon Charles Gibson et al.

It is certified that error appears in the above-identified patent and that said Letters Patent is hereby corrected as shown below:

Title page,  
Item [57], ABSTRACT,  
Line 9, "PR³to" should read -- PR³, subject to --.

Column 27,  
Line 61, "primary secondary" should read -- primary, secondary --.

Column 28,  
Line 29, "pyridine CoCl₂;" should read -- pyridine.CoCl₂; --

Signed and Sealed this

Third Day of August, 2004

JON W. DUDAS  
*Acting Director of the United States Patent and Trademark Office*